(12) United States Patent
Bibian et al.

(10) Patent No.: US 8,798,735 B1
(45) Date of Patent: *Aug. 5, 2014

(54) METHOD AND APPARATUS FOR THE ESTIMATION OF ANESTHETIC DEPTH USING WAVELET ANALYSIS OF THE ELECTROENCEPHALOGRAM

(75) Inventors: Stéphane Bibian, Vancouver (CA); Tatjana Zikov, Shaker Heights, OH (US); Guy Albert Dumont, Vancouver (CA); Craig Robert Ries, Vancouver (CA); Ernest Puil, Vancouver (CA); Hossain Cyrus Ahmadi, Vancouver (CA); Mihai Huzmezan, Vancouver (CA); Bernard Ansell Macleod, Vancouver (CA)

(73) Assignee: Bionova Technologies Inc., Vancouver (CA)

( * ) Notice: Subject to any disclaimer, the term of this patent is extended or adjusted under 35 U.S.C. 154(b) by 1251 days.

This patent is subject to a terminal disclaimer.

(21) Appl. No.: 12/584,083

(22) Filed: Aug. 31, 2009

Related U.S. Application Data

(63) Continuation of application No. 12/148,151, filed on Apr. 17, 2008, now Pat. No. 7,603,168, which is a continuation of application No. 10/616,997, filed on Jul. 11, 2003, now Pat. No. 7,373,198.

(60) Provisional application No. 60/395,313, filed on Jul. 12, 2002.

(51) Int. Cl.
*A61B 5/00* (2006.01)

(52) U.S. Cl.
USPC .......................................... 600/544

(58) Field of Classification Search
CPC ............ A61B 5/04012; A61B 5/4821; A61B 5/7257; A61B 5/726; A61B 5/0476; A61B 5/0488; A61B 5/0435
USPC .................................................. 600/544, 545
See application file for complete search history.

(56) References Cited

U.S. PATENT DOCUMENTS

| 6,042,548 | A * | 3/2000 | Giuffre ........................ 600/483 |
| 7,603,168 | B2 * | 10/2009 | Bibian et al. .................. 600/509 |
| 2004/0010203 | A1 * | 1/2004 | Bibian et al. .................. 600/544 |
| 2005/0137494 | A1 * | 6/2005 | Viertio-Oja ................... 600/544 |
| 2009/0005696 | A1 * | 1/2009 | Riftine ......................... 600/515 |

* cited by examiner

*Primary Examiner* — Michael Kahelin
*Assistant Examiner* — Karen Toth

(57) ABSTRACT

A method and apparatus to monitor the neurologic state of a patient undergoing general anesthesia is provided. Previous automated systems to monitor the neurologic state of a patient undergoing general anesthesia involve a significant time delay between the patient's true hypnotic state and the computed indices. The present invention reduces this time delay by using a different analysis technique applied to spontaneous EEG. A wavelet decomposition and statistical analysis of the observed EEG is conducted and compared to reference data to provide a numerical indicator. In addition, this indicator is more consistent with the patient's loss of consciousness indicated by the loss of count event than previous systems.

21 Claims, 7 Drawing Sheets

METHOD AND APPARATUS FOR THE ESTIMATION OF ANESTHETIC DEPTH USING WAVELET ANALYSIS OF THE ELECTROENCEPHALOGRAM

CROSS-REFERENCE TO RELATED APPLICATIONS

This application is a continuation of U.S. patent application Ser. No. 12/148,151, filed on Apr. 17, 2008 and which issued as U.S. Pat. No. 7,603,168 on Oct. 13, 2009, which is a continuation of U.S. patent application Ser. No. 10/616,997, which was filed on Jul. 11, 2003 and which issued as U.S. Pat. No. 7,373,198 on May 13, 2008, and which claims priority from U.S. Provisional Patent Application Ser. No. 60/395,313 filed Jul. 12, 2002.

BACKGROUND OF THE INVENTION

The present invention relates to the field of clinical anesthesia, in particular to the intraoperative and postoperative monitoring of patients' hypnotic and cognitive states.

The state of anesthesia is achieved by administering a combination of various anesthetic agents that render patients unconscious and insensitive to the trauma of surgery, while providing surgeons with a quiet surgical field. The concept of anesthesia, in the context of modern practice of balanced anesthesia, is a multi-component entity comprising hypnosis, analgesia and muscle relaxation. Thus the term "depth of anesthesia", or "anesthetic depth", is relevant for each of these components measured separately.

All general anesthetics lead to the loss of consciousness. At higher doses they also provide analgesia and muscle relaxation—two clinical end-points that can be independently achieved by analgesics and muscle relaxants. However, these drugs do not provide unconsciousness at clinical concentrations. Hence, although the mechanisms of anesthesia are still largely unknown, it is believed that hypnosis—i.e. drug-induced loss of consciousness and amnesia—is one of its major components.

Traditionally, anesthesiologists titrate drugs by assessing the anesthetic/hypnotic state of a patient based on observations of various clinical signs and their changes (such as blood pressure, heart rate, pupil dilatation, sweating, lacrimation, movement etc.). However, these signs may not always be readily available, and furthermore, may be unreliable. The need for a monitor of hypnosis is especially strengthened by the use of neuromuscular blockade agents in modern clinical practice. It is therefore possible for a patient to be aware of the surgery, yet unable to communicate his or her awareness by movement to the anesthesiologist. Therefore, a monitor of hypnosis/consciousness will provide anesthesiologists with a guide for the precise titration of anesthetic drugs, thus avoiding both overdosing and intraoperative awareness. It is expected that a better titration will result in fewer side effects, faster discharge from intensive care unit, and long term savings in terms of the drug quantities administered during surgeries.

All hypnotic drugs depress the Central Nervous System (CNS). Therefore it is natural to assume that Electroencephalographic (EEG) changes in the brain's electrical activity carry relevant information about drug effects on the brain. Thus, the hypnotic state of a patient could, theoretically at least, be quantified by observing variations in EEG waveforms.

Numerous studies have explored this field since the first observation of the effect of narcotics or general depressant drugs on the EEG in the late 1930's. However, the interpretation of the unprocessed or raw EEG signal is very complex, time consuming and requires an experienced specialist. Therefore, many efforts have been put into deriving EEG-based indices that correlate with the hypnotic state of a patient.

A number of inventions related to monitoring of anesthesia using electroencephalographic signals have already been disclosed.

In John, U.S. Pat. No. 4,557,270 issued Dec. 10, 1985 and U.S. Pat. No. 5,699,808 issued Dec. 23, 1997, systems monitoring patients in postoperative care units are disclosed. These prior art systems are based on Brainstem Auditory Evoked Potentials (BAER) and Brainstem Somatosensory Evoked Potentials (BSER) which are extracted from the EEG signals after an auditory or somatosensory stimulus has been delivered to the patient. The use of such signals suffers from a rather cumbersome setup and the heavy preprocessing of the EEG in order to extract the small evoked signals of interest from the background EEG. These systems also acquired other physiological quantities such as temperature, blood pressure, heart rate, etc.

Another invention using evoked potentials is described in John, U.S. Pat. No. 6,067,467 issued May 23, 2000. This invention further relies on the relative power in the theta band from 3.5 Hz to 7.5 Hz, which is used as an indication of blood flow and pain. A scoring algorithm is used to classify the patient's hypnotic state. The preferred embodiment for this invention is the closed-loop control of anesthetics drugs. A similar concept of closed-loop anesthesia using auditory evoked potentials is disclosed by Mantzaridis et al., international publication number WO 98/10701 published Mar. 19, 1998.

The use of time domain methods and frequency analysis to derive a number of parameters from spontaneous EEG has been thoroughly investigated. In Kangas, U.S. Pat. No. 5,775,330 issued Jul. 7, 1998, the inventor discloses such a technique to classify hypnotic states during clinical anesthesia. This prior art system further relies on a neural network to reach a single univariate descriptor. Maynard, U.S. Pat. No. 5,816,247 issued Oct. 6, 1998, also uses a similar analysis and a neural network for the classification of sleep states. Finally, in Schultz, U.S. Pat. No. 6,011,990 issued Jan. 4, 2000, an autoregressive model of the EEG supplements the spectral analysis. A multivariate classification function is further used to generate an appropriate index representative of the patient's hypnotic state.

Ennen, U.S. Pat. No. 6,317,627 issued Nov. 13, 2001, also uses spectral analysis. However, the disclosed invention uses additional observers that are further combined into a univariate index using component analysis.

Higher order spectral analysis has generated interest since the early 1990's. Chamoun, U.S. Pat. No. 5,320,109 issued June, 1994, and U.S. Pat. No. 5,458,117 issued Oct. 17, 1995, uses bispectral analysis combined with classical spectral analysis to derive an index of hypnosis. This invention's output is a weighted sum of different parameters that are mainly derived using spectral and higher order spectral analysis.

In Merilainen, WO 01/24691 published Sep. 30, 2000, the inventor discloses a system that measures the patient's brain activity by means of a light directed towards the patient's forehead. The light is filtered by the patient's tissues and the analysis of the resulting optical signal gives an indication of the patient's cerebral state.

Finally, in Vierto-Oja, WO 02/32305 published Apr. 25, 2002, the inventor uses the entropy of patients' EEG to ascertain their cerebral state. In one embodiment, the inventor combines a parameter obtained from spectral analysis of the Electromyogram (EMG) to provide a fast indication of change of the patient's state.

While spectral and higher order spectral analysis are the key techniques used in the prior art to provide an accurate and reliable index of hypnosis, clinical practice has shown that some delay exists between the change of the patient's anesthetic state and the changes in the indices that are available today. Although the disclosed techniques of Chamoun and Ennen are already being used with success in the operating room, an index reacting more quickly to changes in a patient's state is desirable. This is particularly true in the context of closed-loop anesthesia where a fast index will increase the stability of the system, hence allowing for better performance. Spectral and high order spectral analyses are particularly suited for signals with repetitive patterns. However, the electroencephalogram is typically a noise-like signal that does not exhibit observable patterns.

The use of auditory or somatosensory evoked potentials has also been thoroughly investigated by the research community. These potentials are particular patterns embedded in the electroencephalogram itself, and resulting from the external excitation of sensory functions. These patterns are clearly different whether the sensory information can be processed by cognitive functions (e.g., awake patient) or not (e.g., anesthetized patients). However, the analysis of these signals suffers from poor signal to noise ratio. Hence, considerable averaging is necessary to extract these potentials, which makes this technique unreliable in detecting rapid changes in patients' state.

Wavelets have generated great interest in the biomedical field. Their very low computational complexity associated with excellent joint time-frequency resolution properties makes them particularly well suited for the analysis of time-varying, non-stationary signals such as the EEG. Wavelets have been successfully used as a diagnostic tool to capture small-scale transients and events within the EEG, as well as to extract various features and waveform patterns from the EEG. Also, wavelets have been used in pre-processing of the EEG, when used as input signal to a neural network, and for the de-noising and compression of EEG data. However, no prior patent addresses the use of wavelet analysis in the context of spontaneous EEG analysis and diagnosing for clinical anesthesia.

Gillberg, international publication no. WO 00/69517, published Nov. 23, 2000 proposes the analysis of heart rhythms using wavelet analysis applied to electrocardiogram (ECG) signals. The digitized signals are analyzed by transforming them into wavelet coefficients by a wavelet transform. The higher amplitude coefficients are identified, selected and compared with pre-defined sets of wavelet coefficients, which are derived from signals of heart rhythms of known type. This method is used to discriminate normal from abnormal rhythms.

The object of the present invention is the use of wavelet analysis to extract a univariate feature from a spontaneous EEG signal that correlates to the patient's hypnotic state (referred to throughout this patent as WAVelet index), hence avoiding the complex and time consuming discriminant analysis and/or neural network training done in previous work.

Furthermore, previous systems are characterized by a significant time delay between the patient's true hypnotic state and the computed indices. This time delay is either the result of the analysis technique itself—such as in spectral and higher order spectral analysis—or the consequence of the large averaging needed in case of evoked potential analysis. Therefore, it is the object of the present invention to significantly reduce this time delay by using a different analysis technique applied to spontaneous EEG. This makes of the WAV a more precise feedback quantity for the monitoring, and/or manual/automatic control of anesthesia.

Finally, while previous systems rely on extensive tuning based on a large number of experimental data, it is an object of this invention to develop a method for diagnosing patients' hypnotic state which does not require neither a large subject pool, nor an extensive database of clinical EEG data.

BRIEF SUMMARY OF THE INVENTION

The present invention provides a method and apparatus for the discrimination between various levels of a patient's hypnotic/consciousness state during general anesthesia. More particularly, the invention provides a method for extracting information from an observed signal representing measured brain activity of a subject in order to evaluate the state of the CNS of the subject comprising:
  a) acquiring a plurality of reference signals, each reference signal corresponding to a distinct CNS state obtained from a reference subject or subjects;
  b) selecting a transformation function which, when applied to one of the reference signals or observed signal, yields a set of coefficients;
  c) selecting a statistical function which, when applied to the set or subset of coefficients derived from one of the reference signals, yields a reference data set which characterizes the corresponding distinct CNS state;
  d) applying the transformation and statistical function to the plurality of reference signals to produce a plurality of reference data sets which distinguish between the corresponding distinct CNS states;
  e) observing the brain activity of the subject to produce the observed signal;
  f) applying the transformation and statistical function to the observed signal to produce an observed data set;
  g) comparing the observed data set to one or more of the reference data sets; and
  h) computing a numerical value or values representative of the subject's CNS state which results from the above comparison.

Preferably this is achieved by means of a wavelet transform based method for analyzing the patient's EEG signal, which is disclosed within this invention. This signal can be acquired using any existing EEG recording device. The invention also provides a computer program product and a system for carrying out the foregoing method.

BRIEF DESCRIPTION OF THE DRAWINGS

In drawings which illustrate a preferred embodiment of the invention.

DETAILED DESCRIPTION OF THE INVENTION

Wavelet Analysis

Overview and Terminology

For better understanding of the detailed description of the invention, it is necessary to present a wavelet analysis overview and terminology.

Wavelet analysis represents a signal as a weighted sum of shifted and scaled versions of the original mother wavelet, without any loss of information. A single wavelet coefficient is obtained by computing the correlation between the scaled and time shifted version of the mother wavelet and the analyzed part of a signal. For efficient analysis, scales and shifts take discrete values based on powers of two (i.e., the dyadic decomposition). For implementation, filter bank and quadrature mirror filters are utilized for a hierarchical signal decomposition, in which a given signal is decomposed by a series of low- and high-pass filters followed by downsampling at each stage, see FIG. 4. This analysis is referred to as Discrete Wavelet Transform (DWT). The particular structure of the filters is determined by the particular wavelet family used for data analysis and by the conditions imposed for a perfect reconstruction of the original signal.

The approximation is the output of the low-pass filter, while the detail is the output of the high-pass filter. In a dyadic multiresolution analysis, the decomposition process is iterated such that the approximations are successively decomposed. The original signal can be reconstructed from its details and approximation at each stage (e.g., for a 3-level signal decomposition, a signal S can be written as S=A3+D3+D2+D1), see FIG. 5. The decomposition may proceed until the individual details consist of a single sample. The nature of the process generates a set of vectors (for instance $a_3$, $d_3$, $d_2$, and $d_1$ in the three level signal decomposition), containing the corresponding coefficients. These vectors are of different lengths, based on powers of two, see FIG. 4. These coefficients are the projections of the signal onto the mother wavelet at a given scale. They contain signal information at different frequency bands (e.g., $a_3$, $d_3$, $d_2$, and $d_1$) determined by the filter bank frequency response. DWT leads to an octave band signal decomposition that divides the frequency space into the bands of unequal widths based on powers of two, see FIG. 6.

The Stationary Wavelet Transform (SWT) is obtained in a similar fashion, however, the downsampling step is not performed. This leads to a redundant signal decomposition with better potential for statistical analysis. The frequency space division is the same as for DWT, see FIG. 6.

Figure 4:
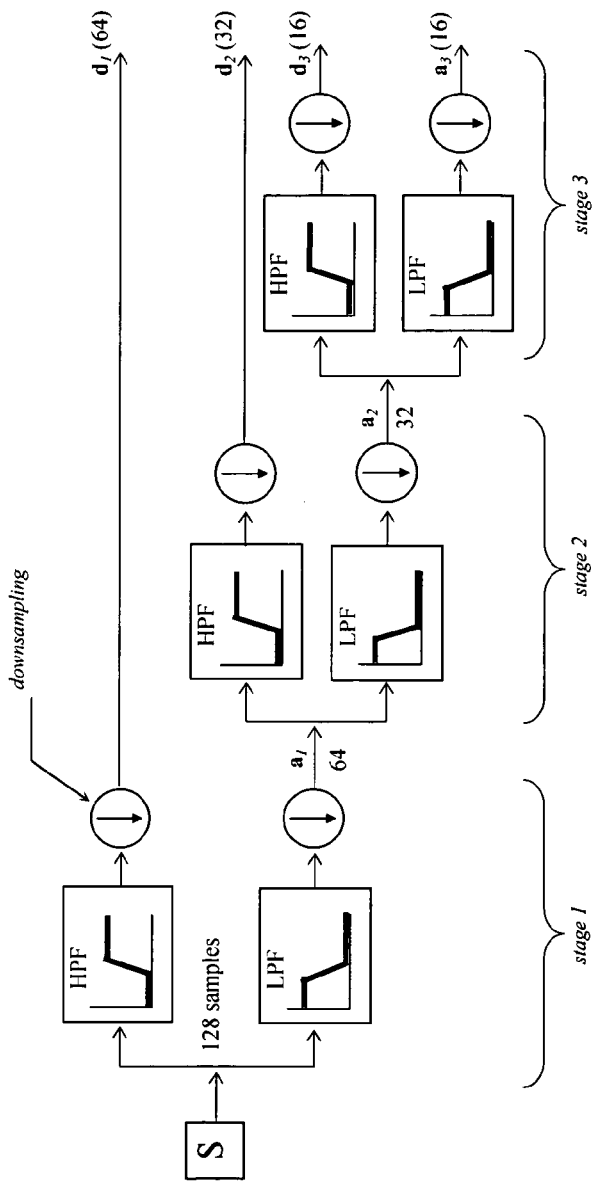
FIG. 4 is a schematic diagram illustrating a 3-level Discrete Wavelet Transform (DWT) filter bank.
Figure 5:
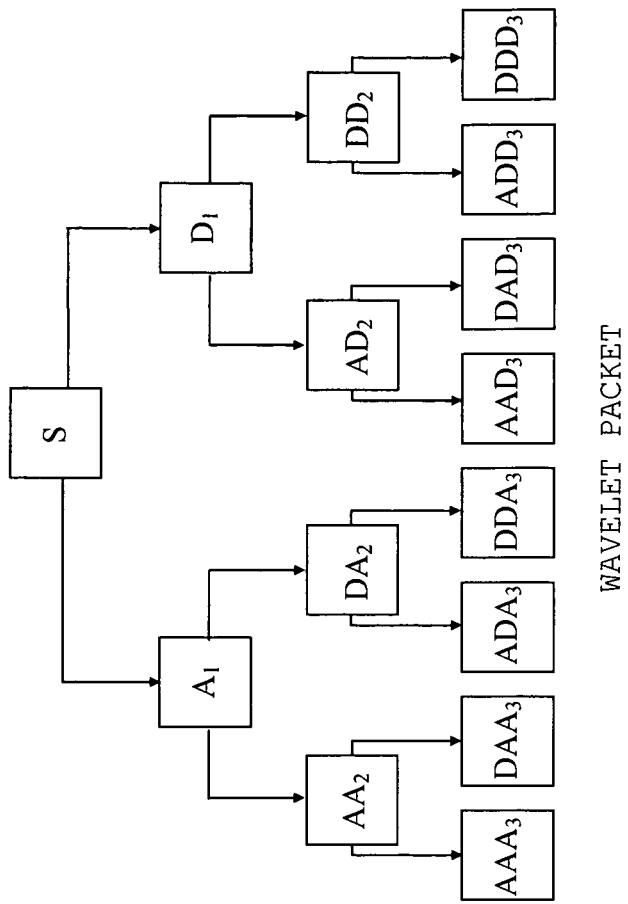
FIG. 5 is an analysis tree (approximations and details) for DWT/Stationary Wavelet Transform (SWT) and wavelet packet decomposition.
Figure 5:
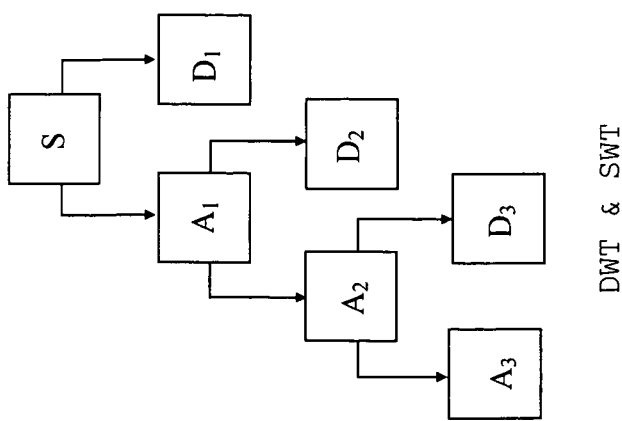
Figure 6:
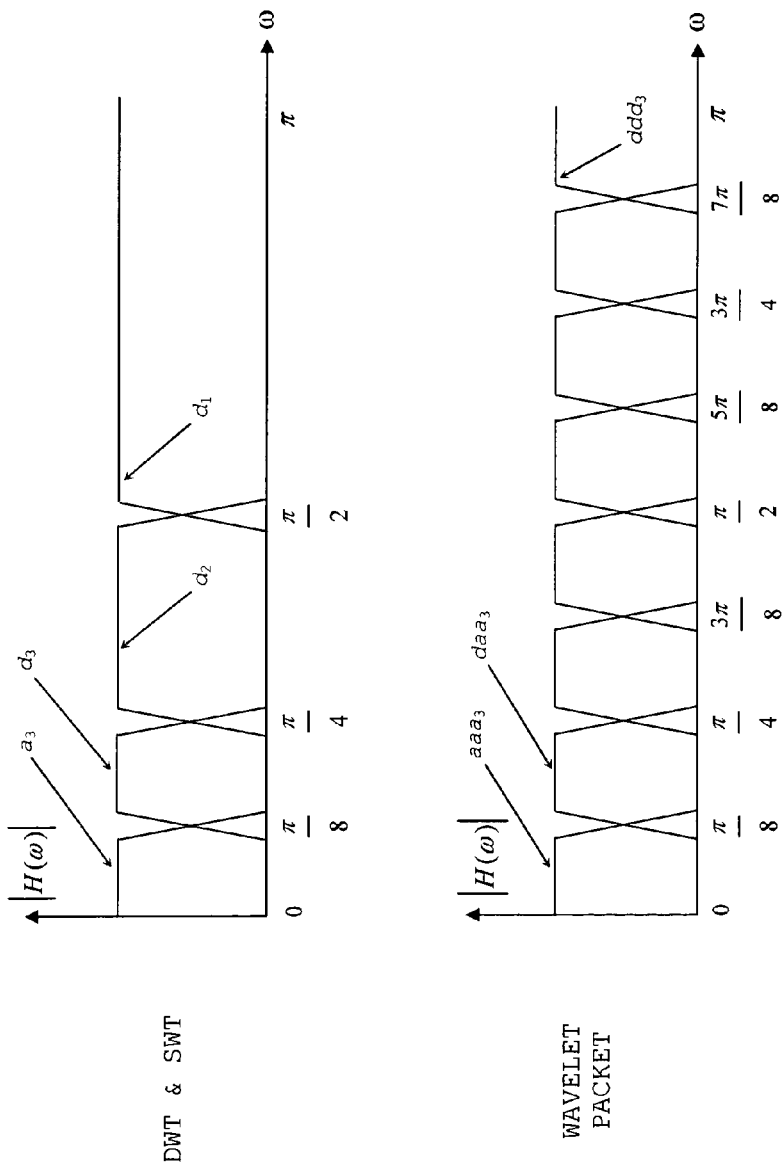
FIG. 6 illustrates the frequency bands for the analysis tree shown in FIG. 5.

Despite its high efficiency for signal analysis, DWT and SWT decompositions do not provide sufficient flexibility for a narrow frequency bandwidth data analysis (FIG. 4.*a*). Wavelet packets, as a generalization of standard DWT, alleviate this problem. At each stage, details as well as approximations are further decomposed into low and high frequency signal components. FIG. 4.*b* shows the wavelet packet decomposition tree. Accordingly, a given signal can be written in a more flexible way than provided by the DWT or SWT decomposition (e.g., at level 3 we have S=A1+AD2+ADD3+DDD3, where DDD3 is the signal component of the narrow high frequency band $ddd_3$). Wavelet packet analysis results in signal decomposition with equal frequency bandwidths at each level of decomposition. This also leads to an equal number of the approximation and details coefficients, a desirable feature for data analysis and information extraction. FIG. 6 illustrates frequency bands for the 3-level wavelet packet decomposition.

Method for the Estimation of the Hypnotic State Using Wavelet Analysis of the EEG This invention relies on the wavelet decomposition of the electroencephalogram (EEG) recorded from a subject. Specifically in our application wavelets were adopted due to their suitablity for the analysis of non-stationary or transitory features, which characterize most signals found in biomedical applications. Wavelet analysis uses wavelets as basis functions for signal decomposition. Wavelet analysis can be viewed as a generalization of Fourier analysis since it introduces time localization in addition to frequency decomposition of a signal. Instead of Fourier analysis which discards time information, wavelets are capable of capturing signal features such as small-scale transients, breakpoints, discontinuities as well as general trends and self-similarity. These features cannot be measured by classical spectral techniques. In addition, wavelets—classes of wave-like functions with a finite number of oscillations, an effective length of finite duration and no offset component—form a basis for the lossless decomposition of a given signal.

In the present invention the use of wavelet transform significantly reduces the computational complexity when performing the task of assessing the subjects' hypnotic state (i.e., level of consciousness) based on their acquired EEG signal. Neither a large number of reference signals nor an extensive amount of clinical EEG data is needed to produce the index of hypnosis disclosed herewith. The methodology of the present invention may also be used to ascertain the state of the brain and the well being of the CNS beyond ascertaining the effects of anesthetic agents on the brain. It may also be used to discriminate between different sleep stages, to assess alertness/drowsiness levels in subjects performing safety critical activities, to evaluate cognitive states such as postoperative and ICU-related cognitive impairment or Alzheimer-related impairment, to detect pre-ictal patterns in order to predict epileptic seizures, to predict seizure duration such as in Electro Convulsive Therapy, to recognize various pathological states of the CNS such as sleep disorders, depression, addiction, ADHD or other pscychiatric disorders, to monitor the changes in the cerebral metabolic rate, to establish the blood characteristic at the cortical level, to obtain pharmacodynamic models of anesthetic and other neurologic and psychoactive drugs, or to develop titration and dosing profiles for such drugs. The preferred embodiment disclosed below is directed towards the assessment of the patient's hypnotic/consciousness level during general anesthesia.

This invention involves an observed data set acquired in real-time from a subject's EEG. This data set is further compared, in real time, with one or more reference data sets which characterize distinct hypnotic states. The comparison yields an index of consciousness/hypnosis that is later referred to WAVelet index (abbreviated WAV). The WAVelet index can then be used to assist in distinguishing the various stages of general anesthesia, in distinguishing increasing and decreasing depths of general anesthesia, and in detecting the loss of consciousness during the induction of general anesthesia, thus providing an endpoint for individual titration of intravenous induction agents.

The observed and reference data sets are statistical representations of the wavelet coefficients obtained by applying a wavelet transform onto corresponding observed and reference signals. These coefficients may be obtained through a wavelet transform of the EEG such as standard dyadic discrete wavelet transform (DWT), discrete stationary wavelet transform (SWT), or wavelet packet transform. In this respect, filters yielding coefficients in a frequency band, chosen such that their statistical representation differentiates between hypnotic states, can be used for this type of analysis. Also, other transforms such as Short Time Fourier Transform (STFT), SLEX transform (Smooth Localized Complex Exponentials) or other transforms providing both time and frequency localization would yield satisfactory results. The choice of this tranformation determines the computational complexity of the method and the resolution of the final index. The observed and reference data sets are obtained by calculating a statistical representation of the transformation coefficients. The methodology of this invention may also be used for extracting information from other physiological signals, such as Electrocardiogram (ECG), representing measured cardiac activity of a subject in order to evaluate the state of the autonomous nervous system of the subject.

The reference data sets represent distinct hypnotic states taken from the continuum from conscious (i.e., fully awake) to isoelectric EEG (i.e., no more brain activity). They are extracted off-line from a group of subjects or patients. They are then stored for real-time implementation. The transformation selected maximizes the dissimilarity between each of the reference data sets.

The comparison between the observed data set against the reference data sets can be based on the computation of the correlation between these functions. However, a computationally less demanding solution is to quantify the similarity between these functions by computing the L1 (Manhattan), L2 (Euclidean), or any distance metrics. In the preferred embodiment, where two reference data sets are used, the result of this comparison yields two values, each expressing the likelihood of a patient being awake or anesthetized. These two values are further combined into a single value corresponding to a univariate index of hypnotic/consciousness state, the WAVelet index.

In the following, a more detailed description of the method for obtaining the hypnotic state of the patient is presented in its preferred embodiment.

Figure 1:
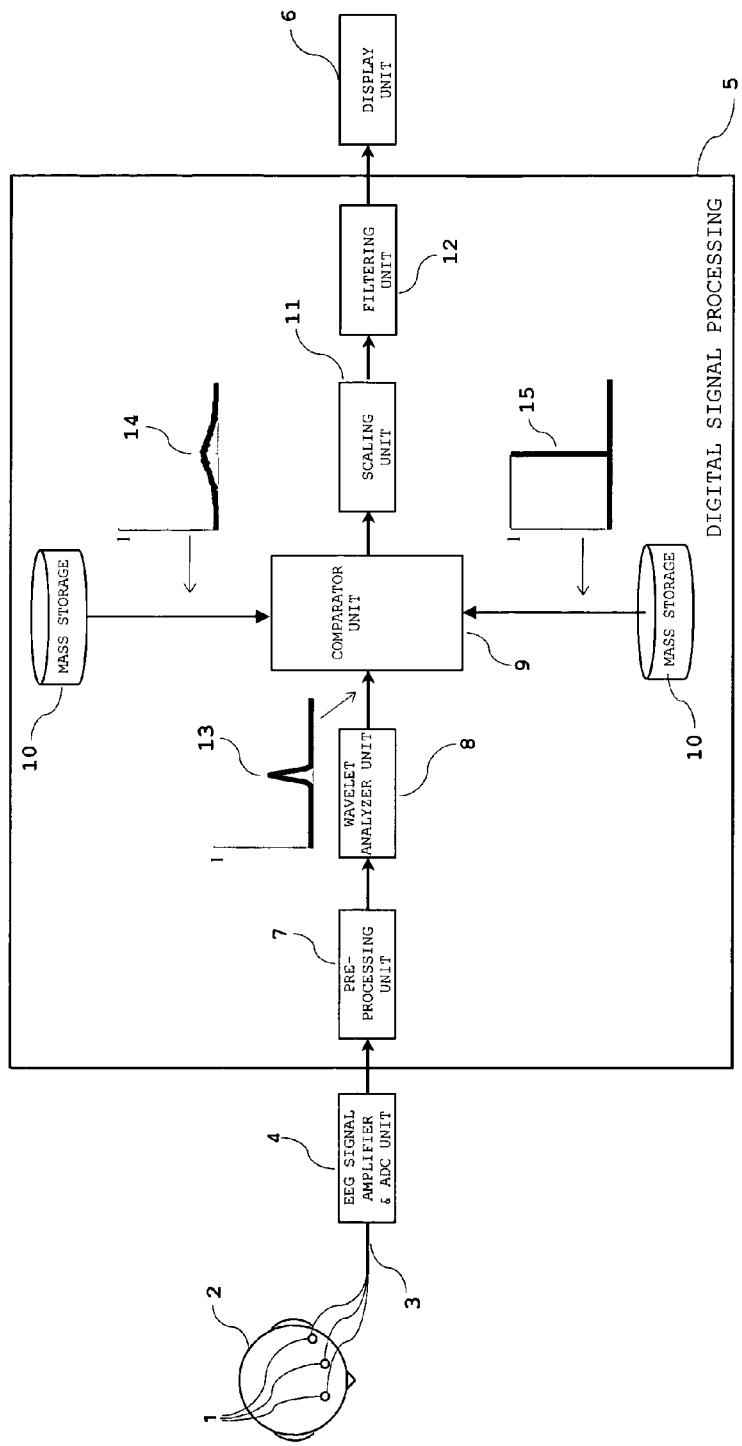
FIG. 1 is a schematic diagram of the apparatus of the invention for estimating the hypnotic state based on wavelet analysis.

FIG. 1 gives an overview of the present invention in its preferred embodiment. The invention is based on the wavelet decomposition of the EEG epoch in the wavelet analyzer unit 8. This unit 8 applies the wavelet transform onto the epoch delivered by the preprocessing unit 7, and then extracts the observed data set 13 correlated to the hypnotic state from the corresponding wavelet coefficients. This feature function is further delivered to the comparator unit 9, where it is compared with two reference data sets 14, 15 corresponding to the known hypnotic states—awake and deeply anesthetized. These reference data sets are calculated off-line and stored in 10 for the real time comparison in the comparator 9. The result of comparison is further integrated into an index of hypnosis, which is the input of the scaling 11 and filtering 12 units. Finally, the output of unit 12 is displayed by display unit 6.

To produce the awake reference signal, an EEG signal acquired from an awake subjects is used. This signal was pre-filtered to reject very low frequency components and very high frequencies, as well as the eventual electromagnetic interference due to the mains using a notch filter. The second reference signal is an isoelectric EEG signal corresponding to the deepest anesthetic state achievable. This signal can be either synthesized on a computer, or directly acquired from a subject exhibiting no brain activity. Epochs of a fixed duration $T_e$ were digitized by an Analog/Digital Converter (ADC), and acquired at a fixed sampling rate $f_s$.

Both reference signals contained M epochs with $N = f_s \cdot T_s$ samples and no apparent artifacts. These two signals form two training data sets that carry sufficient information to discriminate the awake baseline state from the anesthetized state. These data sets can be written as:

$$\begin{cases} T_w = \{x_{w,k}, k = 1, 2 \ldots M\} & \text{(awake)} \\ T_a = \{x_{a,k}, k = 1, 2 \ldots M\} & \text{(anesthetized)} \end{cases} \quad (1)$$

where the vectors $x_{\bullet,k}$ contain N samples representing the $k^{th}$ epoch of either the awake or anesthetized data set. Subscripts w and a stand for "awake" and "anesthetized" states, respectively. To characterize the data sets, a particular feature can be extracted from each epoch. The feature extraction function, $f$ is defined as:

$$f: x_{\bullet,k} \to f(x_{\bullet,k}) = f_{\bullet,k} \quad (2)$$

Each epoch $x_{\bullet,k}$ is associated with a feature $f_{\bullet,k}$. This feature can be either a scalar or a vector. Then, a particular state is characterized by averaging the set $f_{\bullet,k}$ over the corresponding training data set. This results in two averaged features $\overline{f_w}$ and $\overline{f_a}$ defined as:

$$\begin{cases} \overline{f_w} = \dfrac{1}{M} \cdot \sum_{k=1}^{M} f_{w,k} \\ \overline{f_a} = \dfrac{1}{M} \cdot \sum_{k=1}^{M} f_{a,k} \end{cases} \quad (3)$$

These are representatives of the awake and the anesthetized state. In order to assess the hypnotic state of a patient, it is sufficient to record the patient's EEG and calculate the feature $f$ for each epoch. Comparing this value to $\overline{f_w}$ and $\overline{f_a}$, it is possible to calculate the likelihood for the patient to be either awake or anesthetized. Hence, two indexes $i_w$ (awake) and $i_a$ (anesthetized) are defined such that:

$$\begin{cases} i_w = \|f - \overline{f_w}\|_1 \\ i_a = \|f - \overline{f_a}\|_1 \end{cases} \quad (4)$$

where the norm $\|\bullet\|_1$ is defined as:

$$\|x\|_1 = \sum_{j=1}^{N} |x_j| \quad (5)$$

The norm $\|\bullet\|_1$ accurately quantifies the difference between $f$ and $\overline{f}$, by integrating the distance between the two vectors. Higher degree norms can be used for this analysis, or the correlation function between two vectors. However, they would emphasize large differences and lead to a noisier index.

The main difficulty is obviously the selection of an appropriate function $f$. As mentioned in the previous section, each EEG epoch can be decomposed using SWT into a set of coefficients $a$ and $d_j$:

$$x \to \{\{a; d_j\}, j = 1, 2 \ldots L\} \quad (6)$$

where L is the level of decomposition. Each vector $d_j$ represents the detail of the signal in a specific frequency band $d_j$, and the vector a represents the signal approximation at the highest level of decomposition. As for the feature used to characterize each EEG epoch, the Probability Density Function (PDF) of a chosen wavelet detail band $d_j$ is selected:

$$f: x \to f(x) = f = \text{PDF}(d_j) \quad (7)$$

This choice is motivated by the fact that the probability density function does not emphasize large nor small coefficients but, conversely, tends to focus more on the general content of each wavelet decomposition band. This property is indeed used when dealing with noise-like signals such as the EEG.

Another difficulty arises when selecting an appropriate wavelet filter and choosing the best detail coefficient vector $d_j$ for carrying out the analysis. To compare the effectiveness of different wavelets, it is necessary to introduce the discrimination parameter D:

$$D = \|\overline{f_a} - \overline{f_w}\|_1 \quad (8)$$

The discrimination parameter, D, quantifies the difference between $\overline{f_w}$ and $\overline{f_a}$. Obviously, to better distinguish between the awake and anesthetized states, we need to maximize D, i.e., select the wavelet filter and coefficient band that gives the highest value for D.

Figure 7:
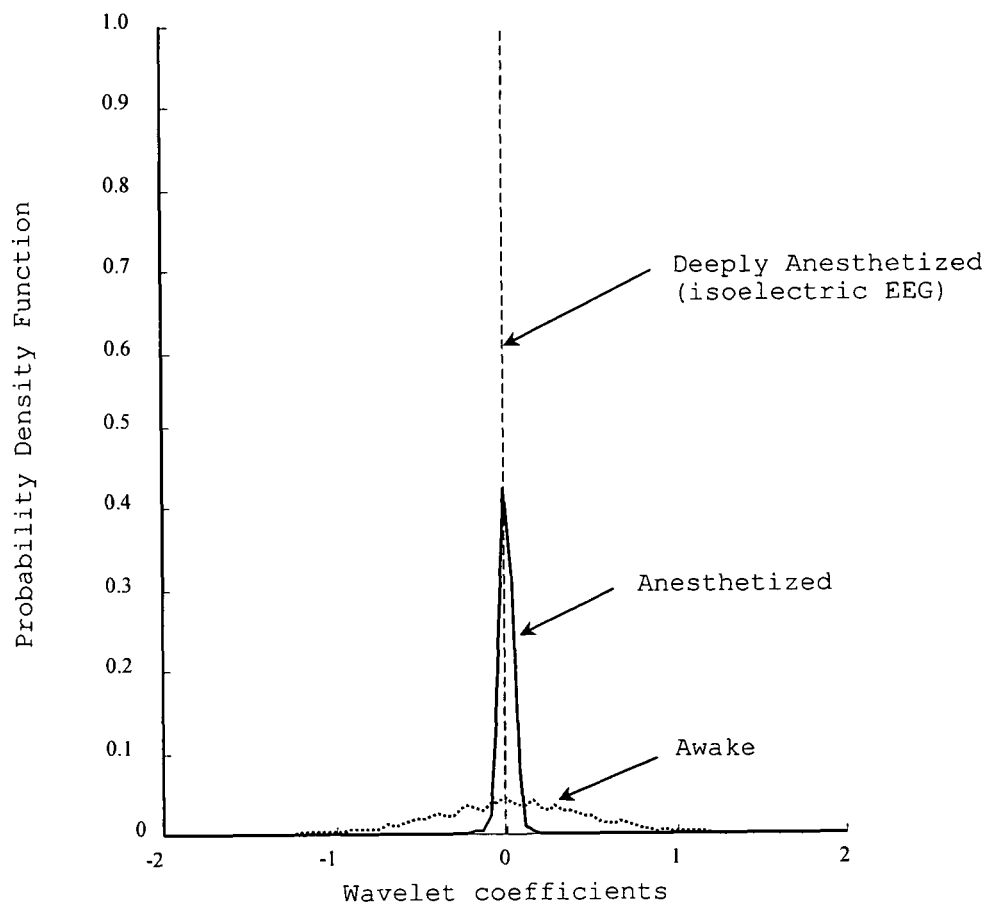
FIG. 7 illustrates the reference data sets for the awake, anesthetized and deeply anesthetized (isoelectric EEG) states using the $d_1$ band and the Daubechie #14 wavelet filter.

The wavelet selection method has been applied to training data sets obtained from awake subjects and anesthetized patients. The sets have been processed to derive the averaged features $\overline{f_w}$ and $\overline{f_a}$ and D. Using as an example a 128 Hz sampling frequency, the analysis using DWT and SWT and the Daubechies wavelet family has clearly singled out the probability density function of the band $d_1$ as the most discriminating. This result is interesting since the $d_1$ band corresponds to the detail in the 32-64 Hz frequency range of the EEG signal. In neurophysiology, this particular frequency band, referred to as the γ-band, often is discarded in classical power spectral analysis since it carries a very small amount of the EEG energy. FIG. 7 illustrates the reference data sets characterizing the awake and anesthetized states.

A similar conclusion using wavelet packets can be reached. Using a 3-level decomposition, the selection for the best wavelet yielded the band $dda_3$ (48-56 Hz) as the most discriminating, in conjunction with the wavelet filter Daubechies #8.

In the preferred embodiment, the signal is decomposed using the SWT, and the 32-64 Hz band is selected, along with the Daubechies #14 wavelet.

Apparatus for the Estimation of the Hypnotic State Using Wavelet Analysis of the EEG While any EEG channel would be suited for the analysis, the electrodes 1 are preferably placed on the patient's 2 forehead. This implementation allows for a greater ease of use. Another reason is that the frontal and prefrontal lobes (which are at the origin of higher cognitive functions) are located directly behind the forehead.

Two electrodes, with a third electrode as a common reference, form a single frontal EEG channel. This signal is input 3 into the amplifier and an Analog/Digital Converter (ADC) unit 4. After amplification, the signal is pre-filtered to reject low frequency components (e.g. <0.5 Hz) and very high frequencies (e.g. >100 Hz), as well as the eventual electromagnetic interference due to the power network (typically 50 Hz or 60 Hz) using a notch filter.

EEG epochs of a fixed duration $T_e$ are digitized by the ADC and acquired at a fixed sampling rate $f_s$. In the preferred embodiment, the epoch length is typically 1 second and sampled at a frequency of 128 Hz. While it is possible to sample the signal at a higher sampling rate, the use of lower sampling rates is not recommended.

Digitized epochs containing $N = f_s \cdot T_s$ samples are then input, one at the time, into the digital signal processing unit 5, where the WAVelet index is calculated in real time by means of a wavelet analysis based method. This resulting index is further displayed by the display unit 6.

All parts of the digital signal processing unit 5 are detailed in the following.

Pre-Processing Unit

Figure 2:
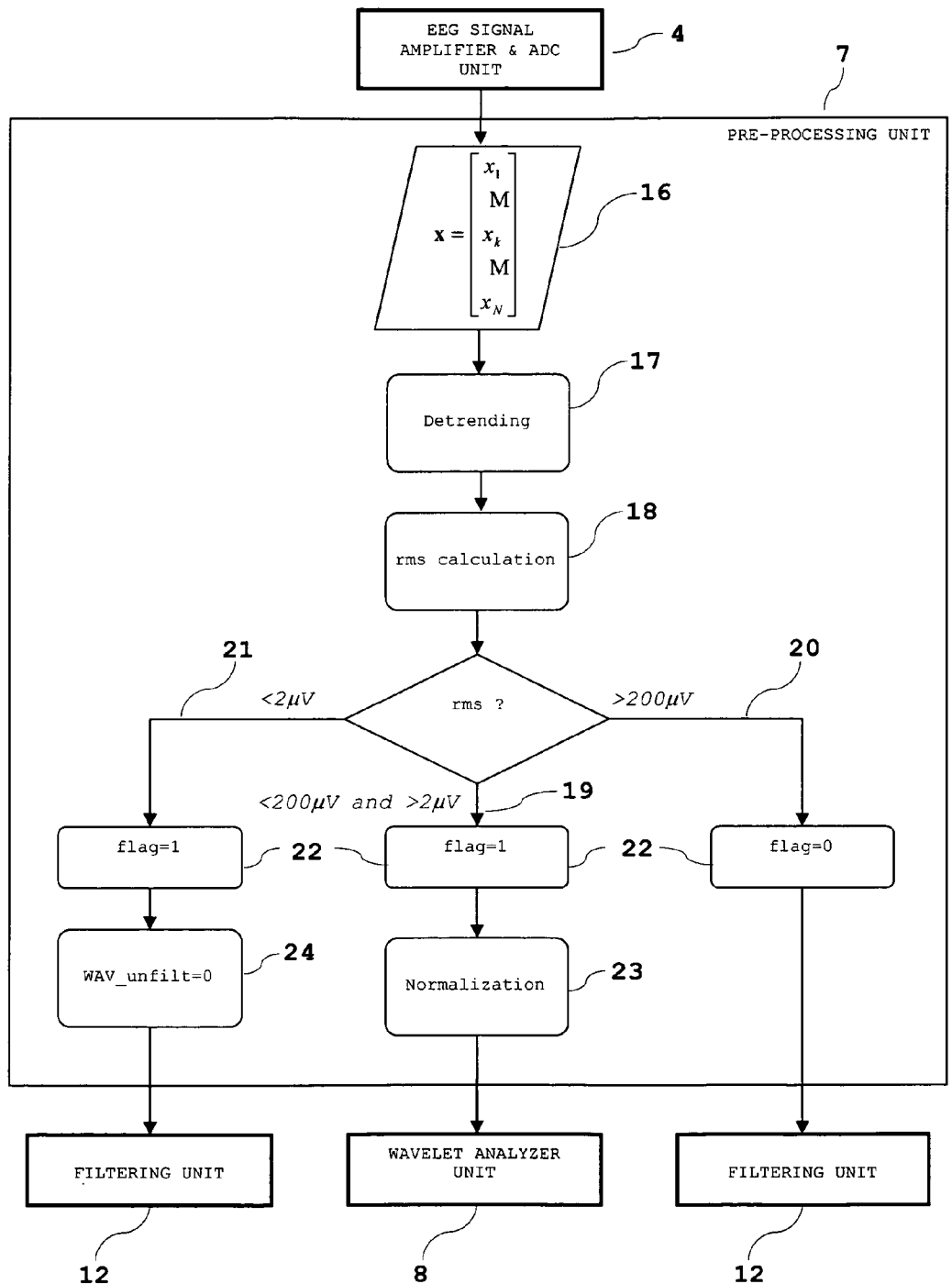
FIG. 2 is a flow chart illustrating the pre-processing function.

Once an epoch has been acquired, it is sent to the pre-processing unit, see FIG. 2. It is first stored as a vector x 16 of length N. The mean value $$\bar{x} = \sum_{k=1}^{N} x_k$$

is removed 17. This offset is due to the signal acquisition process as the EEG is a zero-mean signal. The root mean square amplitude 18 of the epoch is then calculated as:

$$\text{rms} = \sqrt{\frac{1}{N} \cdot \sum_{k=1}^{N} (x_k)^2} \quad (9)$$

Epochs with amplitudes greater than some maximum value (e.g. 200 μV) and less than some minimum value (e.g. 2 μV) are then rejected. It is indeed assumed that they contain either artifacts such as ocular and electrocautery artifacts or isoelectric EEG. If the amplitude is within the two bounds 19, a flag 22 indicating that the epoch is not corrupted takes the value 1. In this case, the epoch is normalized 23 as:

$$x_k = \frac{x_k}{\text{rms}}, k = 1, \ldots, N \quad (10)$$

The amplitude normalization allows better focus on the phase and frequency content of the EEG, rather than its amplitude. Also, this eliminates the influence of electrodes' impedance on the calculation of the index.

The apparatus then proceeds to the next stage, (i.e. the wavelet analyzer unit denoted by 8 in FIG. 1).

If an artifact is present 20, the flag is put to 0 and the algorithm proceeds to the scaling unit 11.

If an isoelectric EEG is detected 21, it is indicative that the patient is in the deepest level of hypnosis. Hence the flag takes the value 1 and the variable WAV_unfilt 24 takes the value of 0. The apparatus then proceeds to send the signal to the filtering unit 12.

Note that the pre-processing unit 7, may also utilize more sophisticated artifact removal methods, such as described in Zikov et al. (T. Zikov, S. Bibian, G. A. Dumont, M. Huzmezan, C. R. Ries, "Wavelet Based De-Noising Technique for Ocular Artifact Correction of the Electroencephalogram," *Proceedings of the 24th Annual International Conference of the IEEE Engineering in Medicine and Biology Society*, Houston, Tex., October 2002).

Wavelet Analyzer Unit

After the pre-processing stage, the input of the wavelet analyzer unit 8 is a normalized epoch (rms amplitude of 1) that does not contain any large artifacts.

The wavelet analyzer unit 8 first calculates the wavelet coefficients applying the SWT and the wavelet filter Daubechies #14 to the pre-processed EEG epoch. The coefficients are obtained by convolution of the EEG epoch with the wavelet filter.

The coefficients corresponding to the band selected in the off-line analysis as the most discriminating (in this embodiment: $d_1$ are then stored in a vector C. The probability density function is then obtained by calculating the histogram of the coefficients in vector C. The vector of histogram contains b coefficients, where b is chosen number of bins (e.g. 100). Each element of this vector is then divided by the total number of coefficients in $d_1$ band, i.e. by the length of a vector C. The result is a vector pdf of length b, which represents the probability density function of wavelet coefficients in $d_1$ band obtained by the wavelet decomposition of the epoch x.

Comparator Unit

Figure 3:
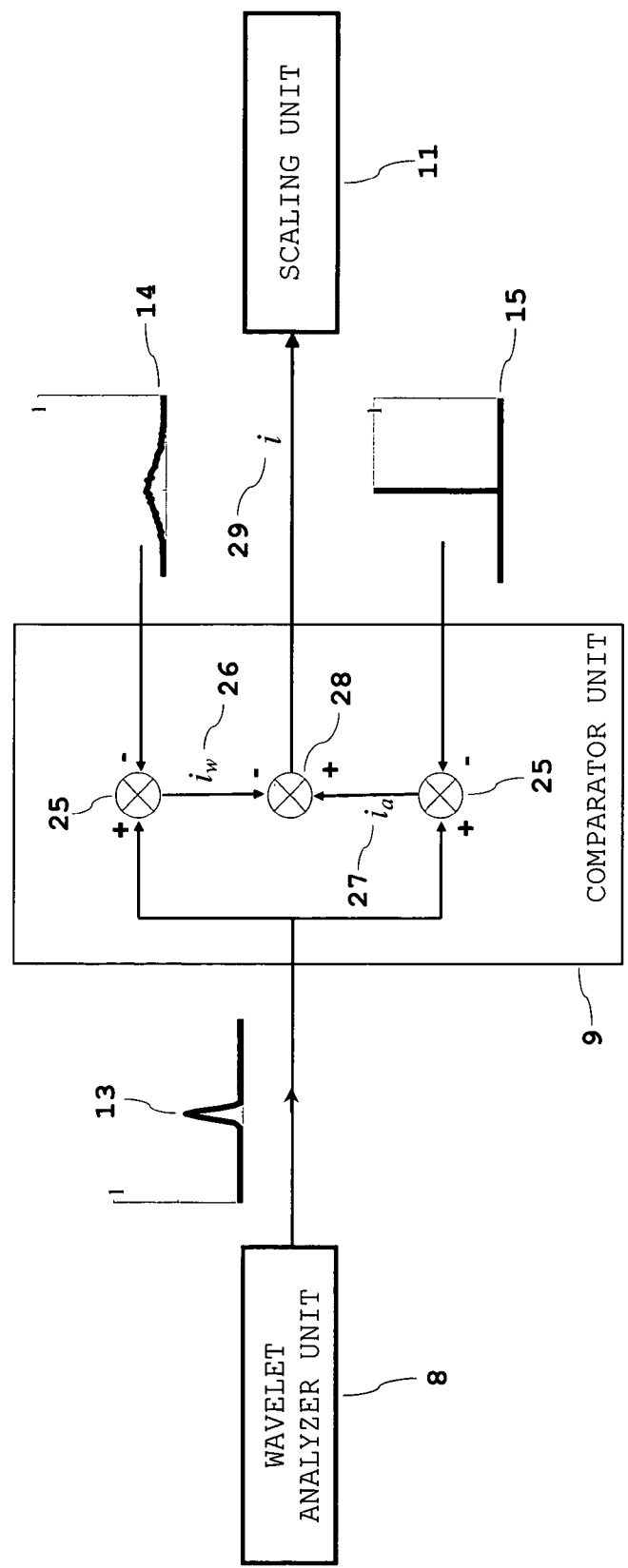
FIG. 3 is a schematic diagram illustrating the comparator function.

The resulting pdf vector is input into comparator unit 9, see FIG. 3. This unit compares the pdf vector of a current epoch 13 with two reference vectors $pdf_w$ and $pdf_a$ representing two known hypnotic states awake 14 and anesthetized 15.

The awake reference data set 14 is derived from a combination of EEG signals obtained from a group of healthy awake subjects (population norming). This reference data set can be then stored on a mass storage device for future real time comparison. Another possibility is to record the patient's EEG while the patient is still awake, and then derive the awake reference data set (self-norming).

The anesthetized reference data set 15 is the PDF of the wavelet coefficients of an isoelectric signal, which corresponds to the deepest level of hypnosis. All coefficients are equal to 0. Hence, this particular PDF is a Dirac function centered at the origin.

The comparison 25 between the pdf 13 calculated in the wavelet analyzer unit 8 and the two reference data sets $pdf_w$ 14 and $pdf_a$ 15 is achieved using the L1 distance metric. This comparison yields two values $i_w$ 26 and $i_a$ 27 calculated as:

$$\begin{cases} i_w = \frac{1}{N} \cdot \sum_{k=1}^{b} |pdf_k - pdf_{w,k}| \\ i_a = \frac{1}{N} \cdot \sum_{k=1}^{b} |pdf_k - pdf_{a,k}| \end{cases} \quad (11)$$

where $pdf_k$, $pdf_{a,k}$ and $pdf_{w,k}$ denote the $k^{th}$ elements of the vectors pdf, $pdf_w$, and $pdf_a$ respectively.

An index i 29 is then generated by calculating 28 the difference between $i_w$ 26 and $i_a$ 27:

$$i = i_a - i_w \quad (12)$$

The output of the comparator unit is then input to the scaling unit 11.

Scaling Unit

The index i is scaled in order to take values between 0% (corresponding to isoelectric signal) and 100% (corresponding to the awake baseline) with higher values indicating higher level of consciousness or awareness:

$$i = i \cdot \text{scale} + \text{offset} \quad (13)$$

scale and offset are two fixed values calculated in the offline analysis. In the preferred embodiment, values like scale=30 and offset=56.4 produced the best results. The result of the scaling is further stored into the variable WAV_unfilt 24.

Filtering Unit

The variable WAV_unfilt 24 contains the unfiltered version of the final WAVelet index. The random character of the EEG dictates that in order to extract a meaningful trend of the patient's hypnotic state it is necessary to smooth this variable using a filter.

A new value WAV_unfilt is delivered by the scaling unit 11 for every epoch (i.e. every second in the preferred embodiment). However, note that if the current epoch is corrupted with an artifact (flag=0 22), the variable WAV_unfilt can take an arbitrary value, as it will not be used to derive the final value of the index.

In the preferred embodiment, the variable WAV_unfilt is averaged over the past 30 seconds of data. The result of the averaging filter is stored in the variable WAV. However, when calculating the average, only uncorrupted epochs are taken into account (by investigating the corresponding flag variable).

Furthermore, in order to account for poor signal quality, if more than a certain number of previous epochs during last 30 seconds are corrupted due to numerous artifacts (e.g. 15), the monitor is unable to give an accurate estimate of the patient's hypnotic state. In that case, the variable WAV takes the value −100%.

The output variable WAV of the averaging filter is then sent to the display unit 6. In case of poor signal quality, a message indicating the presence of numerous artifacts is sent to be displayed by the display unit.

Display Unit

The WAV variable is finally displayed to the anesthesiologist using any standard display device (Cathode Ray Tube (CRT), Liquid Crystal Display (LCD), printer, etc. . . . ). In the preferred embodiment, the variable is displayed as a trend, or as a number, and can further be used as a measurement signal in the context of a feedback controller which does not make the object of the current disclosure.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

The invention claimed is:

1. A method for extracting information from an observed electrophysiological signal from a subject in order to evaluate the level of depression of the central nervous system (CNS) of said subject with a processor, said method comprising:
    a) observing the electrophysiological activity of a subject to produce an observed electrophysiological signal;
    b) applying a pre-selected transformation and statistical function to the observed electrophysiological signal to produce an observed data set;
    c) comparing the observed data set to at least two reference data sets; and
    d) computing with a processor a numerical value or values representative of the level of depression of the CNS of the subject, based at least in part on the comparison;
    wherein the at least two reference data sets correspond to distinct CNS states which are two extreme states.

2. The method of claim 1 wherein the observed electrophysiological signal represents measured cortical activity of the subject and comprises one or more electroencephalograms.

3. The method of claim 1 further comprising the step of ascertaining the level of consciousness of the subject based at least in part on the comparison.

4. The method of claim 1 wherein further comprising the step of ascertaining the effects of anesthesia and anesthetic agents on the CNS of the subject based at least in part on the comparison.

5. The method of claim 1 further comprising the step of ascertaining titration and dosage profiles of anesthesia and anesthetic compounds, gas, and medicaments based at least in part on the comparison.

6. A method for extracting information from two observed electrophysiological signals from a subject, in order to evaluate the levels of depression of the central nervous system (CNS) and autonomic nervous system (ANS) of said subject with a processor, said method comprising:
   a) observing the CNS electrophysiological activity of a subject to produce a first observed electrophysiological signal;
   b) observing the ANS electrophysiological activity of the subject to produce a second observed electrophysiological signal;
   c) applying a pre-selected first transformation and first statistical function to the first observed electrophysiological signal to produce the CNS observed data set;
   d) applying a pre-selected second transformation and second statistical function to the second observed electrophysiological signal to produce the ANS observed data set;
   e) comparing the CNS and ANS observed data sets to at least one CNS and at least one ANS reference data set, respectively; and
   f) computing with a processor a numerical value or values representative of the levels of depression of the CNS and ANS of the subject, respectively, based at least in part on the comparison
   wherein the at least one CNS reference data set corresponds to a known CNS state, and
   wherein said at least one ANS reference data set corresponds to a known ANS state.

7. The method of claim 6 wherein the first and second observed electrophysiological signals are both EEG.

8. The method of claim 6 wherein the observed electrophysiological signals are electroencephalograms and electrocardiograms.

9. The method of claim 6 further comprising the step of ascertaining the effects of anesthesia agents on the CNS and ANS, respectively, of the subject based at least in part on the comparison.

10. The method of claim 6 further comprising the step of ascertaining titration and dosage profiles of anesthesia compounds and medicaments based at least in part on the comparison.

11. The method of claim 6 further comprising the step of controlling automatically or manually the levels of consciousness and analgesia of the subject based at least in part on the computed numerical value or values representative of the levels of depression of the CNS or ANS of the subject.

12. The method of claim 6 wherein the first and second pre-selected transformation are both joint time-frequency transforms.

13. A method for calculating a filtered index of the level of depression of the central nervous system (CNS) of a subject from an electrophysiological signal with a processor, said method comprising:
   a) observing the electrophysiological activity of a subject using signal acquisition circuitry to produce an observed electrophysiological signal segment;
   b) detecting using a processor the presence of electrocautery artifacts in the observed electrophysiological signal segment;
   c) setting an artifact flag variable to a certain value if one or more electro-cautery artifacts are detected, or to a different value if no artifact is detected;
   d) applying a pre-selected transformation and statistical function to said observed electrophysiological signal segment to produce an observed data set;
   e) comparing the observed data set to at least one reference data set corresponding to a known CNS state;
   f) computing with the processor an unfiltered index of the level of depression of the CNS of the subject based at least in part on the comparison; and
   g) calculating the filtered index of the level of depression by inputting to a filter both the unfiltered index of the level of depression and the artifact flag variable.

14. The method of claim 13 wherein the pre-selected transformation is a joint time-frequency transform.

15. The method of claim 13 wherein the detection of electro-cautery activity is based in part on the amplitude of the observed electrophysiological signal segment.

16. A method for calculating an index of the level of depression of the central nervous system (CNS) of a subject from an electrophysiological signal with a processor, said method comprising:
   a) observing the electrophysiological activity of a subject to produce an observed electrophysiological signal segment;
   b) detecting using a processor the presence of isoelectric activity in the observed electrophysiological signal segment;
   c) if isoelectric activity is detected, setting the index of the level of depression to a pre-defined value; and
   d) if isoelectric activity is not detected:
      i. applying a pre-selected transformation and statistical function to the observed electrophysiological signal to produce an observed data set;
      ii. comparing the observed data set to at least one reference data set corresponding to a known CNS state; and
      iii. computing with the processor the index of the level of depression of the CNS of the subject based at least in part on the comparison.

17. The method of claim 16 wherein the index of the level of depression of the CNS is further filtered to yield a trended index of the level of depression of the CNS.

18. The method of claim 16 wherein the pre-defined value when isoelectric activity is detected is essentially zero.

19. The method of claim 16 wherein the pre-selected transformation is a joint time-frequency transform.

20. The method of claim 16 wherein the detection of isoelectric activity is based in part on the amplitude of the observed electrophysiological signal segment.

21. The method of claim 16 further comprising the step of ascertaining titration and dosage profiles of anesthesia and anesthetic compounds, gas, and medicaments based at least in part on the comparison.

* * * * *